US009931235B2

(12) United States Patent
Summer et al.

(10) Patent No.: US 9,931,235 B2
(45) Date of Patent: Apr. 3, 2018

(54) PASSIVE LOCKING HAND EXOSKELETON (71) Applicant: HARRIS CORPORATION, Melbourne, FL (US)

(72) Inventors: Matthew D. Summer, Melbourne, FL (US); Paul M. Bosscher, West Melbourne, FL (US)

(73) Assignee: Harris Corporation, Melbourne, FL (US)

( * ) Notice: Subject to any disclaimer, the term of this patent is extended or adjusted under 35 U.S.C. 154(b) by 604 days.

(21) Appl. No.: 14/568,563

(22) Filed: Dec. 12, 2014

(65) Prior Publication Data
US 2016/0229635 A1 Aug. 11, 2016

(51) Int. Cl.
A61F 5/01 (2006.01)
(52) U.S. Cl.
CPC .................... A61F 5/013 (2013.01)
(58) Field of Classification Search
CPC ............. A61H 1/0285; A61H 1/0288; A61H 2001/0207; A61H 5/0102; A61H 5/013; A61H 2005/0132; A61H 2005/0137; A61H 2005/0139; A61H 2005/0158; A61F 2/68; A61F 2/583; A61F 5/013
See application file for complete search history.

(56) References Cited

U.S. PATENT DOCUMENTS

| 4,644,941 A * | 2/1987 | Ogle, II | A61F 5/05875 602/22 |
| 4,865,613 A * | 9/1989 | Rizzo | A61F 2/583 623/57 |
| 5,178,137 A * | 1/1993 | Goor | A61F 5/0111 601/40 |
| 5,516,249 A | 5/1996 | Brimhall | |
| 8,255,079 B2 | 8/2012 | Linn et al. | |
| 8,262,599 B2 * | 9/2012 | Chandrasekar | A61F 5/05875 602/20 |
| 2007/0167893 A1 * | 7/2007 | Frisbie | A61F 5/0102 602/12 |
| 2010/0249676 A1 * | 9/2010 | Kawakami | A61F 5/013 601/40 |

(Continued)

FOREIGN PATENT DOCUMENTS

| CN | 102579227 | 1/2014 |
| WO | 2014033613 | 3/2014 |

OTHER PUBLICATIONS

Klauer, C., et al., "Feedback control of arm movements using Neuro-Muscular Electrical Stimulation (NMES) combined with a lockable, pasive exoskeleton for gravity compensation," Frontiers in Neuroscience, published Sep. 2, 2014; DOI:10.3389/fnins.2014. 00262.

Primary Examiner — LaToya M Louis
(74) Attorney, Agent, or Firm — Fox Rothschild LLP; Robert J. Sacco; Carol E. Thorstad-Forsyth (57) ABSTRACT Systems (100) and methods (600) for operating an exoskeleton disposed at least partially on a joint of a wearer's limb (118). The methods involve respectively aligning first apertures (310 or 312) of a first planar flexible element (304 or 306) of the exoskeleton with second apertures (310 or 312) of a second planar flexible element (304 or 306) of the exoskeleton. The first and second planar flexible elements abut each other. A toothed flexible element (302) is then caused to ratchetedly engage the first and second planar flexible elements by bending the joint.

10 Claims, 5 Drawing Sheets (56) References Cited

U.S. PATENT DOCUMENTS

| | | | |
|---|---|---|---|
| 2010/0305717 A1* | 12/2010 | Tong | A61H 1/0285 623/64 |
| 2011/0054371 A1* | 3/2011 | Colditz | A61F 5/0118 602/16 |
| 2012/0059290 A1* | 3/2012 | Yip | A61H 1/0288 601/40 |
| 2012/0059291 A1 | 3/2012 | Nguyen | |
| 2013/0219585 A1 | 8/2013 | Bergelin et al. | |
| 2015/0245972 A1* | 9/2015 | Arakawa | A61H 1/0288 601/40 |

* cited by examiner

PASSIVE LOCKING HAND EXOSKELETON

FIELD OF THE INVENTION

This document relates generally to robotic exoskeletons. More particularly, this document relates to robotic exoskeletons for hands.

BACKGROUND OF THE INVENTION

Robotic exoskeletons provide controlled mobility, as well as an increased strength, endurance, mobility and safety. Robotic exoskeletons are used for healthcare and rehabilitation, human augmentation, and human protection from injury. Rehabilitation/orthotic hand exoskeletons comprise actuators to provide finger guidance/assistance for re-learning movement. Force feedback hand exoskeletons comprise actuators that apply forces to the fingers so as to provide haptic feedback thereto. Grasp assistance hand exoskeletons include actuators that pull on fingers to increase the user's grip strength and decrease hand fatigue. Notably, the actuators of these hand exoskeletons place a relatively large amount of strain on the user's fingers which has the potential to cause injury thereto.

SUMMARY OF THE INVENTION

The present disclosure concerns implementing systems and methods for operating an exoskeleton disposed at least partially on a joint of a wearer's limb. The methods involve respectively aligning first apertures of a first planar flexible element of the exoskeleton with second apertures of a second planar flexible element of the exoskeleton. The first and second planar flexible elements abut each other. A toothed flexible element is then caused to ratchetedly engage the first and second planar flexible elements by bending the joint.

The toothed flexible element ratchetedly engages the first and second planar flexible elements as a result of a sliding movement in a first direction away from the joint by a greater distance than the distance traveled by the first and second planar flexible elements when the joint is bent. In this regard, it should be understood that the first planar flexible element, the second planar flexible element and the toothed flexible element follow a curvature of the joint when the joint is bent. The toothed flexible element is closer to a center of curvature than the first and second planar flexible elements.

Notably, the toothed flexible element is designed such that it is prevented from sliding in a second direction opposed from the first direction when a force is applied to the wearer's limb by an object. However, the toothed flexible element can be disengaged from the first and second planar flexible elements by straightening the joint.

In some scenarios, a latching behavior of the exoskeleton is activated when the first and second apertures are respectively aligned. The first and second apertures are respectively aligned by moving, in a direction towards the joint, a latching disabling mechanism coupled to the first planar flexible element when the joint is in a straight position. The latching behavior of the exoskeleton is deactivated by respectively offsetting the first apertures and the second apertures. The first and second apertures are offset from each other by moving, in a direction away from the joint, a latching disabling mechanism coupled to the first planar flexible element when the joint is in a straight position.

In those or other scenarios, the first planar flexible element, the second planar flexible element and/or the toothed flexible element is(are) prevented from moving radially away from the joint. Alternatively or additionally, current is applied to a shape metal alloy disposed on or adjacent to at least one of the first planar flexible element, the second planar flexible element, and the toothed flexible element when a disengagement of the toothed flexible element from the first and second planar flexible elements is desired.

DESCRIPTION OF THE DRAWINGS

Embodiments will be described with reference to the following drawing figures, in which like numerals represent like items throughout the figures, and in which.

DETAILED DESCRIPTION OF THE INVENTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

Figure 1:
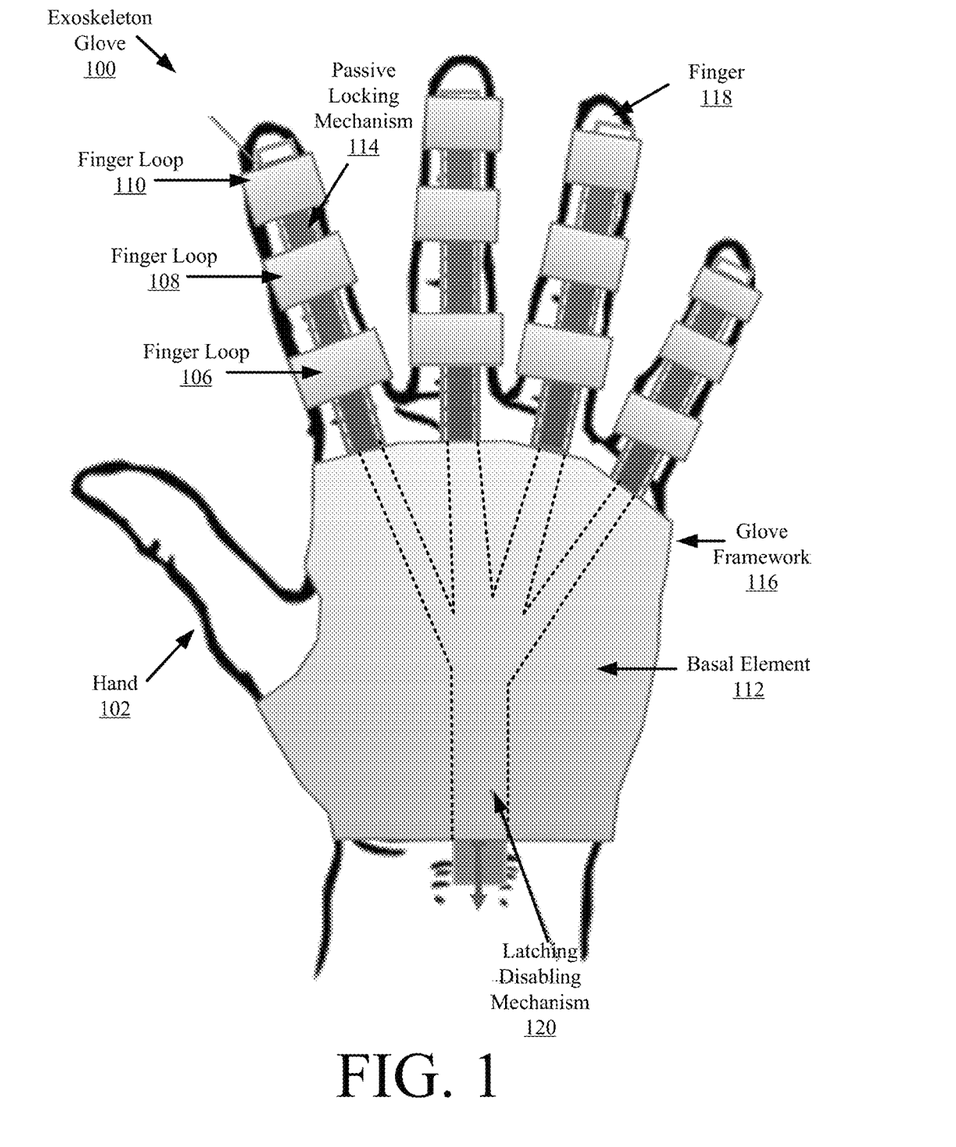
FIG. 1 is a front view of an exemplary exoskeleton glove disposed on a human hand.

Referring now to FIG. 1, there is provided a schematic illustration of an exemplary exoskeleton glove 100. Although the present invention is described herein in relation to an exoskeleton glove arrangement, the present invention is not limited in this regard. The present invention can be used in any exoskeleton application in which a joint is transitioned between a straight position and a bent position. This will become more evident as the discussion progresses.

The exoskeleton glove 100 can be used in many applications. Such applications include, but are not limited to, medical applications (e.g., therapy applications, assistive device applications), domestic applications (e.g., police applications, first responder applications), commercial applications (e.g., human strength/endurance amplification applications), and military applications. Accordingly, the exoskeleton glove 100 may be used to assist the wearer by boosting his(her) strength and/or endurance. The exoskeleton glove 100 may also be designed to help soldiers more firmly grasp and carry heavy loads both in and out of combat. In civilian areas, the exoskeleton glove 100 could be used to help firefighters and other rescue workers survive dangerous environments, as well as to assist nurses with grasping and moving heavy patients.

The exoskeleton glove 100 comprises a glove framework 116 which is fitted to a user's hand 102. The glove framework 116 is provided with a glove-like configuration into which the hand 102 can be inserted and retained therein. In this regard, the glove framework 116 in formed of a basal element 112 and a plurality of finger loops 106, 108, 110. Three finger loops are provided in FIG. 1 for each finger 118 (except for the thumb). The present invention is not limited in this regard. Any number of finger loops can be provided in accordance with a particular application for any number of fingers per hand.

The basal element 112 and the finger loops 106-110 are formed of any suitable material, such as leather, cloth or plastic. In all scenarios, the glove framework 116 engages the hand 102 with sufficient snugness so as to enable a user to control one or more locking mechanisms 114 of the exoskeleton glove 100. Notably, in some scenarios, a locking mechanism 114 is provided for all the user's fingers except for the thumb, as shown in FIG. 1. The present invention is not limited in this regard. A locking mechanism can be provided for one finger, two-four fingers, or all five fingers of a hand.

Each locking mechanism 114 is coupled to the basal element 112 and/or the respective finger loops 106-110 such that it resides in parallel arrangement with the corresponding finger of the hand 102 throughout the entire time in which the exoskeleton glove 100 is being worn by a user thereof. The parallel arrangement facilitates the user's control of the locking mechanism 114 using only the corresponding finger thereof.

Each locking mechanism 114 is passive in operation. The user can selectively enable and disable the passive locking mechanism 114 with his(her) hand 102. As a user closes his(her) hand 102 around an object (not shown), the passive locking mechanism 114 locks into place. The user controls the closed position of each finger 118. The passive locking mechanism 114 resists opening until the user actively opens his(her) hand 102.

Notably, the exoskeleton glove 100 has many advantages. For example, the user can resist very large forces with minimal efforts. Also, the exoskeleton glove 100 is absent of actuators acting on the user's fingers 118 and sensors for sensing the user's intent. As such, the exoskeleton glove 100 is much simpler as compared to conventional exoskeleton gloves, such as those described in the Background Section of this paper. Additionally, the exoskeleton glove 100 can be worn on the palm-side of hand 102 (as shown in FIG. 1) or the backside of hand 102 (not shown). When worn on the palm-side of the hand 102, forces applied to the user's hand is reduced. When worn on the backside of the hand 102, the user can directly feel the environment. Furthermore, the passive locking mechanism 114 is simple to operate. All the user needs to do is close his(her) hand to a desired set-point and open his(her) hand to release the passive locking mechanism 114.

Operations of the passive locking mechanism 114 will now be described in relation to FIGS. 2-5. As shown in FIGS. 2-5, the passive locking mechanism 114 comprises three elongated flexible elements 302, 304, 306 defining a ratcheting mechanism. The flexible elements may be formed of any suitable material, such as a thin sheet of metal which is resilient (e.g., spring-like functionality). Notably, the flexible elements 302, 304, 306 should have a thickness and width that prevents or is rigid in compression when the passive locking mechanism 114 is in use.

The particular arrangement of the three flexible elements 302, 304, 306 is selected such that ratcheting and/or locking of the passive locking mechanism 114 occur(s) in response to the bending of a respective finger 118. The ratcheting and/or locking occur(s) in a manner similar to that of a zip tie, as will be discussed in detail below. In this regard, the planar flexible element 306 is located closest to the finger, while the toothed flexible element 302 is located furthest from the finger.

Figure 4:
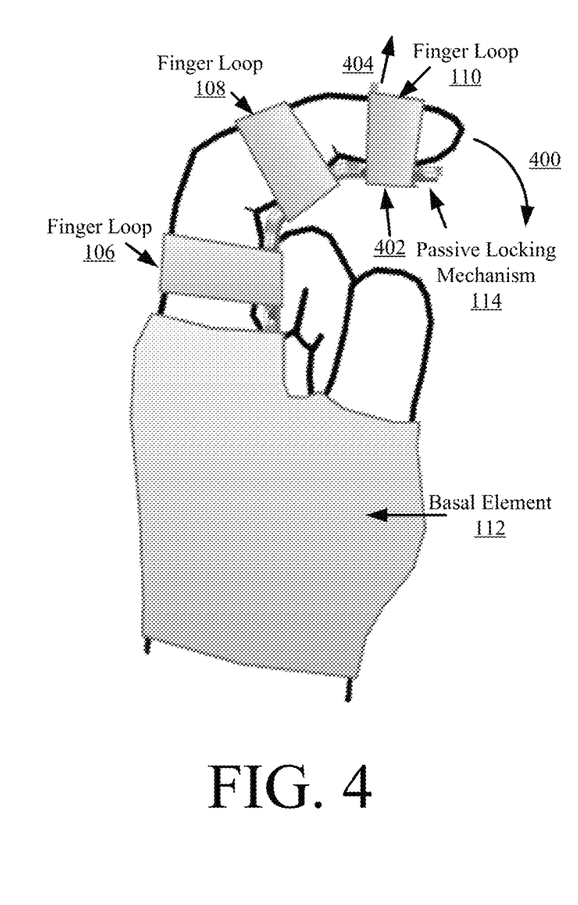
FIG. 4 is a side view of an exoskeleton glove disposed on a human hand with all five fingers bent.
Figure 5:
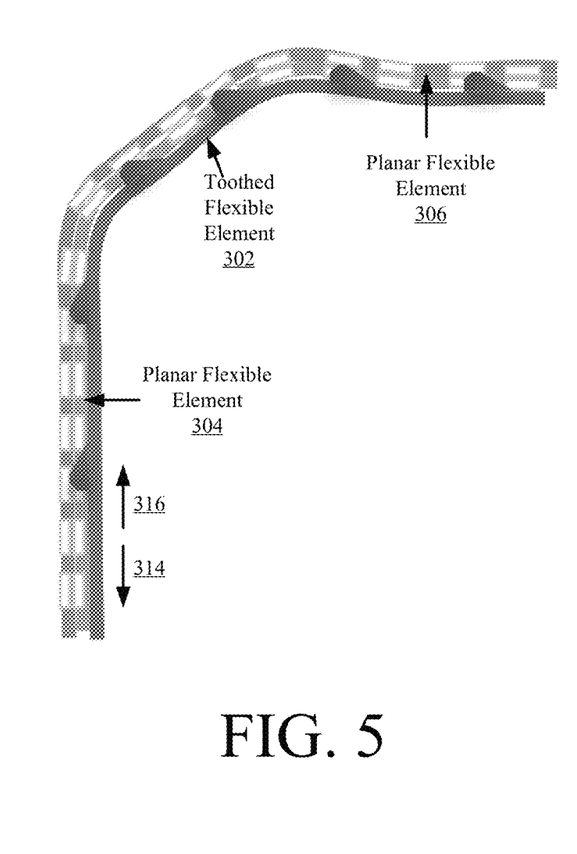
FIG. 5 is a side view of a locking mechanism of the exoskeleton glove shown in FIG. 4.

The planar flexible element 306 is connected to the basal element 112 via a latching disabling mechanism 120. The purpose of the latching disabling mechanism 120 will be discussed below. At this time, it should be understood that if the planar flexible element 306 is pushed down in direction 316 along the length of the respective finger 118 via the latching disabling mechanism 120, the planar flexible element 306 slides in direction 316 without buckling. The stiffness of the planar flexible element 306 also ensures that the planar flexible element 306 will follow the curvature of the respective finger 118 when bent or being bent by the wearer of the exoskeleton glove with a modest amount of effort, as shown in FIG. 4. A plurality of apertures 312 are formed in the planar flexible element 306.

Figure 2:
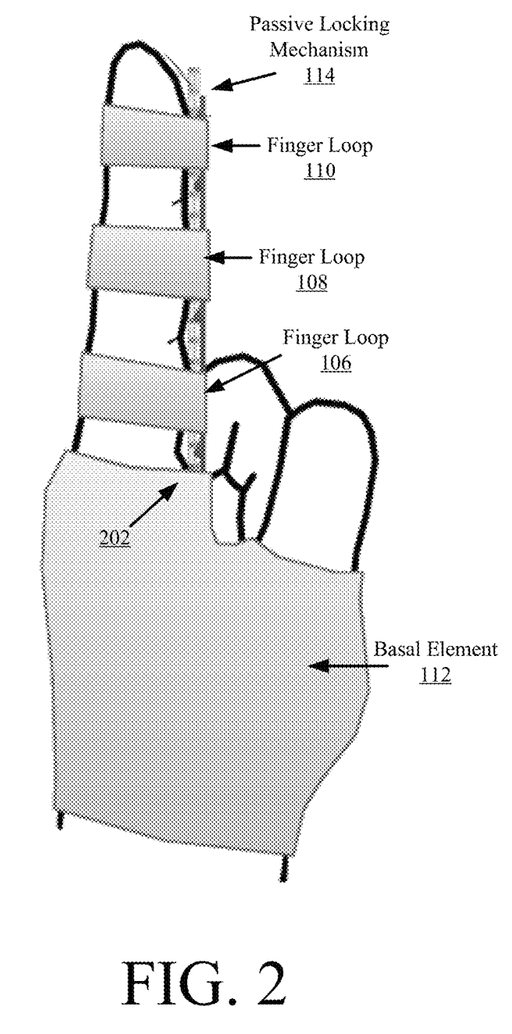
FIG. 2 is a side view of an exoskeleton glove disposed on a human hand with one finger extended and four fingers bent.
Figure 3:
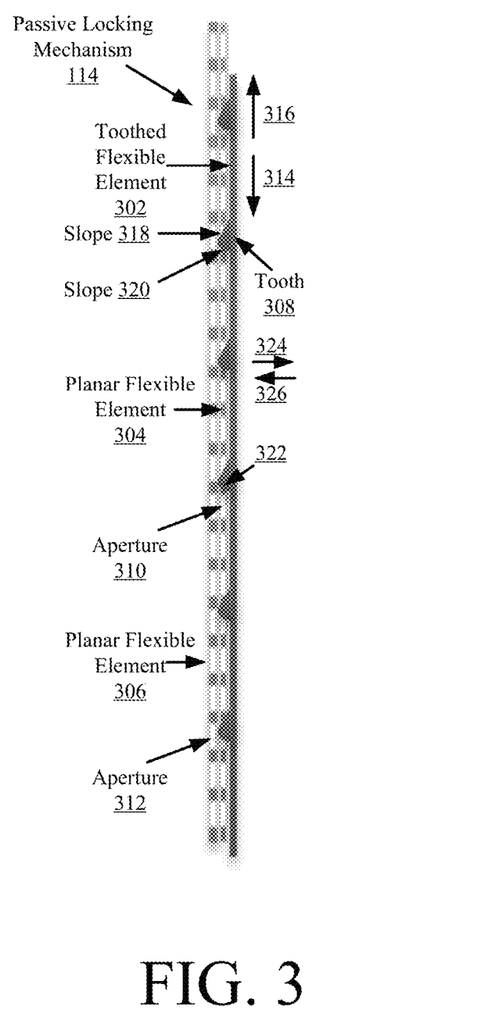
FIG. 3 is a side view of a locking mechanism of the exoskeleton glove shown in FIG. 2.

The planar flexible element 304 is layered on the side of the planar flexible element 306, and is fixedly attached at one end 202 to the glove framework 116. A plurality of apertures 312 are also formed in the planar flexible element 304. The planar flexible elements 304 and 306 are disposed adjacent to one another such that apertures 310 and 312 thereof can be respectively aligned with or offset from each other when the flexible elements are in their straight positions (e.g., as shown in FIG. 2). The planar flexible element 304 has a stiffness that is the same as or similar to that of the planar flexible element 306, such that the planar flexible element 304 does not buckle during use of the exoskeleton glove 100. The stiffness of the planar flexible element 304 also ensures that the planar flexible element 304 will follow the curvature of the respective finger 118 when bent or being bent by the wearer of the exoskeleton glove with a modest amount of effort, as shown in FIG. 4.

Figure 7:
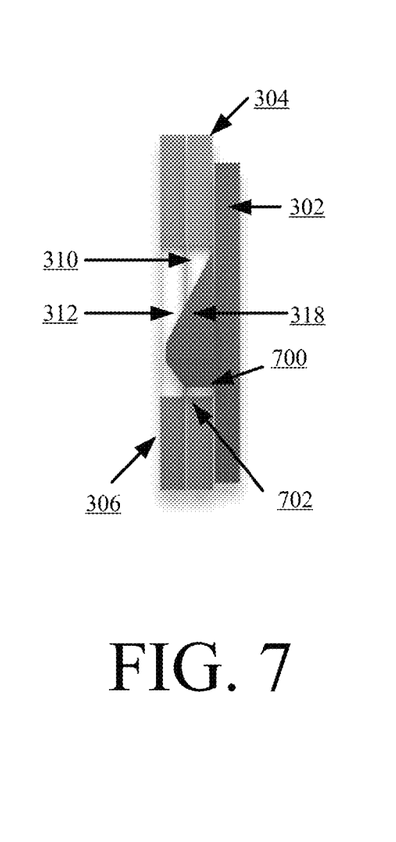
FIGS. 7 and 8 provide schematic illustrations that are useful for understanding operations of a locking mechanism of the exoskeleton glove shown in FIGS. 1-5.
Figure 8:
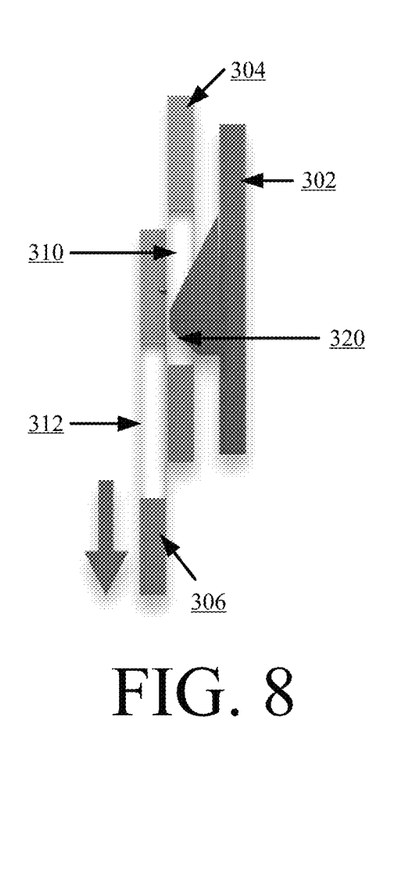

Notably, the two planar flexible elements 304 and 306 and the latching disabling mechanism 120 essentially provide a means for selectively causing the latching behavior of the passive locking mechanism 114 to be transitioned from an inactive (or off) state in which no latching/ratcheting behavior occurs in response to the bending of the finger to an active (or on) state in which the latching/ratcheting behavior occurs in response to the bending of the finger. When the apertures 310 and 312 are respectively aligned with each other as shown in FIG. 7, the passive locking mechanism 114 is in latching mode in which a latching or ratcheting action can occur. In contrast, the passive locking mechanism 114 is not in its latching mode when the apertures 310 and 312 are respectively offset from each other as shown in FIG. 8. The offset arrangement of the apertures 310 and 312 can be selectively achieved by pulling a latching disabling mechanism 120 in a direction down and away from the hand 102. In turn, the aligned arrangement of the apertures 310 and 312 can be selectively achieved by pushing the latching disabling mechanism 120 in a direction towards and into the hand 102, whereby the planar flexible element 306 is pushed in a direction towards the fingers.

The toothed flexible element 302 is layered on the side of the planar flexible element 304, and is fixedly attached at one end 202 to the glove framework 116. The toothed flexible element 302 constitutes a rack with a plurality of teeth. The teeth are uniform but asymmetrical. Each tooth 308 has a moderate slope 318 on one edge and a much steeper slope 320 on the other edge. The teeth are disposed along the entire length of the toothed flexible element 302 in an equally spaced manner.

When the passive locking mechanism 114 is in latching mode, the teeth respectively protrude through apertures 310 and 312 when aligned therewith. The moderate slope 318 of each tooth allows the toothed flexible element 302 to slidingly move relative to the planar flexible elements 304, 306 in a first direction 316. However, a straight sidewall 700 of each tooth's steeper sloped end prevents the tooth from slidingly out of the respective apertures 310, 312 when the toothed flexible element 302 is moved in a second direction 314. In this regard, it should be understood that the straight sidewall 700 abuts a sidewall 702 of the respective aperture 310. The movement of the toothed flexible element 302 is similar to that of a latching toothed portion of a zip tie.

When the passive locking mechanism 114 is not in its latching mode, the teeth respectively only protrude through apertures 310 of the planar flexible element 304 (and not apertures 312 of the planar flexible element 306) when aligned therewith, as shown in FIG. 8. This is because the apertures 310 and 312 are respectively offset from each other. Notably, the tooth's straight sidewall 700 does not abut the sidewall 702 of the respective aperture 310 when the toothed flexible element 302 is moved in the second direction 314. Rather, the tooth's steep slope 320 engages the planar flexible element 304 when the toothed flexible element 302 is moved in the second direction 314, as also shown in FIG. 8. In effect, the tooth is able to slide out of the respective aperture 310 when the toothed flexible element 302 is moved in a second direction 314.

When the wearer of the exoskeleton glove 100 curves his(her) finger 118 as shown in FIG. 4, an arc length situation occurs where the toothed flexible element 302 is closer to the center of curvature then the planar flexible elements 304 and 306. In effect, the toothed flexible element 302 slides out and away from the finger 118 a greater distance than the distance traveled by the other two planar flexible elements 304, 306. Also, the planar flexible element 306 travels relative to planar flexible element 304 such that the apertures 310 and 312 remain aligned with each other when the finger is being bent. As the toothed flexible element 302 travels out and away from the finger, at least one tooth of the flexible element 304 is pushed out of apertures 310-312 in which it resides, and caused to latch into a next aperture thereof. Notably, the toothed flexible element 302 will be prevented from sliding in an opposite direction towards the finger when a force is applied to the finger 118 in a direction 402. So, as long as the wearer is applying a light force to the backside of the passive locking mechanism 114 (enough to keep the teeth in the apertures 310 and/or 312), the passive locking mechanism 114 has a greater stiffness in a direction opposing the load.

If the wearer decides that (s)he would like to release an object, then all (s)he has to do is simply pull back his(her) hand in direction 404. As a consequence of the finger's movement, the planar flexible elements 304 and 306 are pulled in direction 404. This pulling causes the disengagement of the apertures 310, 312 from the teeth of flexible element 302. Once this bond is broken between the flexible elements 302-306, the wearer's hand can be freely opened.

In some scenarios, it may be desirable to disable the ratcheting mechanism of the exoskeleton glove 100 (e.g., while the wearer is tying his(her) shoes or performing other activities). The ratcheting mechanism is disabled by sliding the planar flexible element 306 in direction 314 when the hand is in its straight position such that apertures 310 and 312 are offset from each other. As mentioned above, such disabling is achieved using the latching disabling mechanism 120. In the disabled position, the teeth can move in both directions 314 and 316. When moved in direction 314, the teeth still engage apertures 310, but not apertures 312. However, the teeth are designed to each comprise a steep sloped chamfered tip 322. The chamfered tips 322 allow the teeth of the toothed flexible element 302 to disengage (or slide out of) apertures 312 when the toothed flexible element 302 moves in direction 314, as described above.

In some scenarios, bearing elements (not shown) are provided on the glove framework 116 to capture the flexible elements 302-306 so as to prevent them from moving radially around the finger 118, but still allow the flexible elements 302-306 to move linearly in direction 314 and 316 relative to the finger. The bearing elements can be formed from a low coefficient of friction plastic. The bearing elements may include, but are not limited to, tracks.

As shown in FIG. 1, the planar flexible elements 304 and 306 are wider than toothed flexible element 302. The planar flexible elements 304 and 306 are also designed to be closely disposed adjacent to one another such that no gap exists between these two flexible elements when coupled to the glove framework 116, as shown in FIG. 2. The bearing elements and/or tracks control the relative positioning of the planar flexible elements 304 and 306.

The bearing elements and/or tracks also control the relative positioning of toothed flexible element 302 and the planar flexible element 304. Toothed flexible element 302 needs to be able to move in directions 324 and 326 so that the teeth can engage and disengage apertures 310, 312 during use of the exoskeleton glove 100. As such, the bearing elements and/or tracks control the maximum distance that the toothed flexible element 302 can move in a direction 324 away from the finger.

In some scenarios, the unloaded or neutral position of the flexible elements 302-304 is the straight position shown in FIG. 2. If the finger is curved at all, then the flexible element 302 pushes against planar flexible element 304 since it is trying to return to its straight position. Notably, the spring rates of the flexible element 302-304 are selected such that the teeth can be disengaged from the apertures 310-312 when the finger is transitioned from its curved position (e.g., such as that shown in FIG. 4) to its straight position shown in FIG. 2. In other scenarios, the unloaded or neutral position of the flexible elements 302-304 is a curved position (e.g., such as that shown in FIG. 4 or a less curved position).

In those or other scenarios, a shape memory alloy (not shown) may be employed. The shape memory alloy has a memory of its natural position. The shape memory alloy may be deflected from its natural position to an unnatural position via movement of the wearer's finger. When a current is applied to heat the shape memory alloy, the shape memory alloy will try to actively return to its natural position. In effect, the shape memory alloy can assist the disengagement behavior of the flexible element 302. Depending on the natural position of the shape metal alloy, current can be supplied to heat the shape memory alloy when the wearer desires to transition the passive locking mechanism 114 from a curved position (e.g., that shown in FIG. 3) to a straight position (e.g., that shown in FIG. 2), or vice versa. The shape memory alloy may be disposed on the flexible element 302 at locations other than the teeth locations. Additionally or alternatively, the shape memory alloy may include thin wires spanning the finger's entire length or a portion of the finger's length.

For example, let's assume that a shape metal alloy is disposed on a surface of the toothed flexible element 302 that is opposed from the surface on which the teeth are disposed. The shape metal alloy's natural position is its straight position. As the wearer bends his(her) finger, the toothed flexible element 302 ratchetedly engages the planar flexible elements 304, 306. Also, the shape metal alloy is deflected to a curved position. When the wearer desires to disengage the toothed flexible element 302 from the planar flexible elements 304, 306, (s)he begins moving the finger in a direction to straighten the same. This movement causes the teeth of the toothed flexible element 302 to travel out of the apertures of the planar flexible elements 304, 306. Shortly thereafter, current is applied to the shape metal alloy so as to cause it to actively return to its natural straight position. Notably, the current applied to the shape metal alloy is of a relatively low value which does not cause any harm to the wearer. The present invention is not limited to the particulars of this example.

Figure 6:
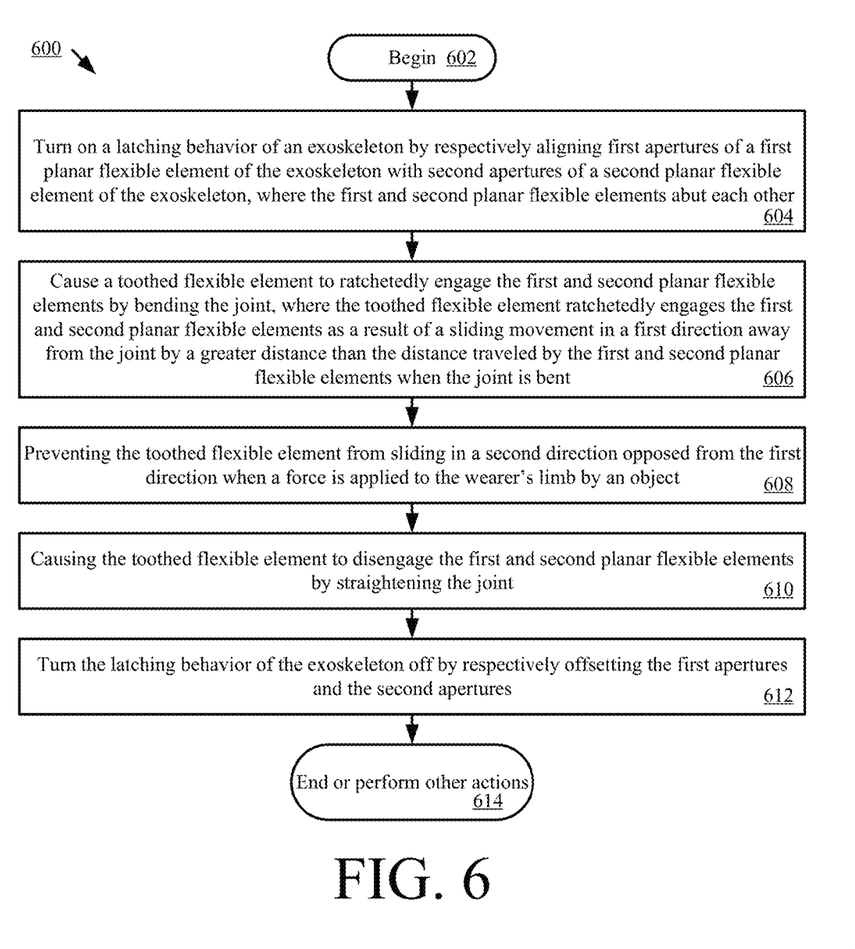
FIG. 6 is a flow diagram of an exemplary method for opening and closing an exoskeleton glove.

Referring now to FIG. 6, there is provided a flow diagram of an exemplary method 600 for operating an exoskeleton (e.g., exoskeleton glove 100 of FIG. 1) disposed at least partially on a joint of a wearer's limb (e.g., finger 118 of FIG. 1). The method 600 begins with step 602 and continues with step 604. In step 604, a latching behavior of the exoskeleton is turned on by respectively aligning first apertures (e.g., apertures 310 of FIG. 3) of a first planar flexible element (e.g., flexible element 304 of FIG. 3) of the exoskeleton with second apertures (e.g., apertures 312 of FIG. 3) of a second planar flexible element (e.g., flexible element 306 of FIG. 3) of the exoskeleton. In some scenarios, the first and second apertures are respectively aligned by moving, in a direction towards the joint, a latching disabling mechanism (e.g., latching disabling mechanism 120 of FIG. 1) coupled to the first planar flexible element when the joint is in a straight position.

Thereafter in step 606, a toothed flexible element (e.g., flexible element 302 of FIG. 3) is caused to ratchetedly engage the first and second planar flexible elements by bending the joint. The toothed flexible element ratchetedly engages the first and second planar flexible elements as a result of a sliding movement in a first direction away from the joint by a greater distance than the distance traveled by the first and second planar flexible elements when the joint is bent. In this regard, it should be understood that the first planar flexible element, the second planar flexible element and the toothed flexible element follow a curvature of the joint when the joint is bent. The toothed flexible element is closer to a center of curvature than the first and second planar flexible elements.

In a next step 608, the toothed flexible element is prevented from sliding in a second direction opposed from the first direction when a force is applied to the wearer's limb by an object (e.g., a rock, a bag, a cup, explosives, etc.). Sometime later, step 610 is performed where the toothed flexible element is caused to disengage the first and second planar flexible elements by straightening the joint.

Once the joint is straightened, the wearer may desire to turn the latching behavior of the exoskeleton off. In this case, step 612 is performed where the latching behavior of the exoskeleton is turned off by respectively offsetting the first and second apertures. The first and second apertures are offset from each other by moving, in a direction away from the joint, a latching disabling mechanism coupled to the first planar flexible element when the joint is in a straight position. Subsequently, step 614 is performed where method 600 ends or other actions are performed.

All of the apparatus, methods, and algorithms disclosed and claimed herein can be made and executed without undue experimentation in light of the present disclosure. While the invention has been described in terms of preferred embodiments, it will be apparent to those having ordinary skill in the art that variations may be applied to the apparatus, methods and sequence of steps of the method without departing from the concept, spirit and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope and concept of the invention as defined.

The features and functions disclosed above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

We claim:

1. A method for operating an exoskeleton disposed at least partially on a joint of a wearer's limb, comprising:
respectively aligning apertures formed in a first planar flexible element of the exoskeleton with through-holes formed in a second planar flexible element of the exoskeleton, where the first and second planar flexible elements comprise two separate elongate planar structures which are positioned so that
(A) a first elongate flat surface of the first planar flexible element abuts a first elongate flat surface of the second planar flexible element, and
(B) a second elongate flat surface of the second planar flexible element, opposed from the first elongate flat surface of the second planar flexible element, resides adjacent to teeth of a toothed flexible element: and
causing the toothed flexible element to ratchetedly engage the first and second planar flexible elements by bending the joint, where
the first planar flexible element, the second planar flexible element and the toothed flexible element follow a curvature of the joint when the joint is bent, and
the toothed flexible element is at a distance from a center of curvature defined by said bending that is different than that of the first and second planar flexible elements.

2. The method according to claim 1, wherein a latching behavior of the exoskeleton is activated when the apertures and through-holes are respectively aligned.

3. The method according to claim 1, wherein the apertures and through-holes are respectively aligned by moving, in a direction towards the joint, a latching disabling mechanism coupled to the first planar flexible element when the joint is in a straight position.

4. The method according to claim 1, wherein the toothed flexible element ratchetedly engages the first and second planar flexible elements as a result of a sliding movement in a first direction away from the joint by a greater distance than the distance traveled by the first and second planar flexible elements when the joint is bent.

5. The method according to claim 4, further comprising preventing the toothed flexible element from sliding in a second direction opposed from the first direction when a force is applied to the wearer's limb by an object.

6. The method according to claim 1, further comprising causing the toothed flexible element to disengage the first and second planar flexible elements by straightening the joint.

7. The method according to claim 1, further comprising deactivating a latching behavior of the exoskeleton by respectively offsetting the apertures and through-holes.

8. The method according to claim 7, wherein the apertures and through-holes are offset from each other by moving a latching disabling mechanism coupled to the first planar flexible element when the joint is in a straight position.

9. The method according to claim 1, further comprising preventing at least one of the first planar flexible element, the second planar flexible element and the toothed flexible element from moving radially away from the joint.

10. A method for operating an exoskeleton disposed at least partially on a joint of a wearer's limb, comprising:
respectively aligning first apertures of a first planar flexible element of the exoskeleton with second apertures of a second planar flexible element of the exoskeleton, where the first and second planar flexible elements abut each other;
causing a toothed flexible element to ratchetedly engage the first and second planar flexible elements by bending the joint, where
the first planar flexible element, the second planar flexible element and the toothed flexible element follow a curvature of the joint when the joint is bent, and
the toothed flexible element is at a distance from a center of curvature defined by said bending that is different than that of the first and second planar flexible elements; and
applying current to a shape metal alloy disposed on or adjacent at least one of the first planar flexible element, the second planar flexible element, and the toothed flexible element when a disengagement of the toothed flexible element from the first and second planar flexible elements is desired.

\* \* \* \* \*